United States Patent [19]

Ishii et al.

[11] 4,096,757
[45] Jun. 27, 1978

[54] METHOD AND APPARATUS FOR EXAMINING WELD DEFECTS IN VERTICAL PIPES BY SUPERSONIC WAVES

[75] Inventors: Ryoichi Ishii; Yoshishige Sakurai; Hiroshi Yamada; Kuniharu Uchida, all of Yokohama; Kanekichi Suzuki, Tokyo, all of Japan

[73] Assignee: Tokyo Shibaura Denki Kabushiki Kaisha, Japan

[21] Appl. No.: 748,370

[22] Filed: Dec. 7, 1976

[30] Foreign Application Priority Data

Dec. 8, 1975  Japan ................... 50-145141
Dec. 8, 1975  Japan ................... 50-145143
Dec. 12, 1975 Japan ................... 50-147422
Dec. 12, 1975 Japan ................... 50-147423

[51] Int. Cl.² ............................................ G01N 29/04
[52] U.S. Cl. ................................. 73/621; 73/623
[58] Field of Search ............ 73/67.8 S, 67.7, 71.5 US

[56] References Cited

U.S. PATENT DOCUMENTS 3,002,375  10/1961  Moffatt et al. ............... 73/67.8 S
3,960,006   6/1976  Smith .............................. 73/71.5 US

FOREIGN PATENT DOCUMENTS 1,600,873  9/1970  France ........................ 73/67.8 S

*Primary Examiner*—James J. Gill
*Attorney, Agent, or Firm*—Stevens, Davis, Miller & Mosher

[57] ABSTRACT

An ultrasonic defect detection apparatus comprising a supersonic probe, a rotary shaft for revolving the probe along the inner surface of a pipe to be examined, and a hollow shaft removably connected to the rotary shaft for vertically moving the probe. Water acting as a contact medium is circulated between the operating surface of the probe and a water tank through the rotary shaft and the hollow shaft. The apparatus is inserted into a pipe to be examined such as the control rod housing of an atomic reactor through the bottom opening of the pipe, and can be operated from a remote place for the sake of safety.

13 Claims, 12 Drawing Figures

METHOD AND APPARATUS FOR EXAMINING WELD DEFECTS IN VERTICAL PIPES BY SUPERSONIC WAVES

BACKGROUND OF THE INVENTION

This invention relates to supersonic apparatus for detecting defects in welded pipes. The apparatus utilizes a probe head provided with a plurality of probes, for example 10, and is inserted in the welded pipe for detecting defects in the weld.

Supersonic detection of defects in metal pipes or the welds thereof is generally carried out from outside of the pipes in the factory of the pipe manufacturer. In certain cases, the defect detecting apparatus is located inside horizontally laid pipes, but it is rare to install the defect detection apparatus in a vertically disposed pipe. In the supersonic defect detection of pipes, water utilized as the contact medium is discarded or circulated through a large tank. Especially, in an atomic power plant, as the quantity of the discarded water is tremendous it is very expensive to treat radioactive substances contained in the spent water so that it is advantageous to install a small tank for recirculating the water. In order to efficiently detect weld defects of various types it is necessary to use not only a vertical defect detection method but also an oblique defect detection method. In the latter method, it is preferred that the angle of inclination can be varied. When a supersonic defect detector is used for a vertical pipe having a length of more than 5 meters, it is necessary to use special devices to mount and dismount the supersonic fault detecting apparatus and the driving shaft of the probe head, so that it is necessary to employ at least several workmen for this purpose.

The accumulated amount of radioactive rays irradiated on workmen operating in an atomic power plant is proportional to the product of the radioactive rays and time so that it is necessary to reduce the working time. However, until today compact and integral supersonic defect detection apparatus has not been used which can be readily mounted and dismounted and which is automatically operable from a remote place. Especially, where such detection apparatus is used in a highly radioactive environment it takes much time to evaluate and analyze the result of the examination where the detection apparatus becomes inoperative also, if a noise echo appears when the detection apparatus is being manually operated by an operator who holds it in his hand, the reliability decreases because the echo resulting from the defect becomes unstable. Since the defects or faults in the pipes or welds thereof must be supervised during the life of the atomic power plant (for example, 40 years) for the purpose of confirming the pipe is safe, it is necessary to reliably perform such supervision by mechanical means.

SUMMARY OF THE INVENTION

It is an object of this invention to provide novel supersonic defect detection apparatus for pipes and welds thereof which is compact, can be readily mounted and dismounted and which can be automatically operated from a remote place.

Another object of this invention is to provide improved supersonic defect detection apparatus for pipes and welds thereof that can be readily mounted and operated inside of the pipes by a single operator.

Still another object of this invention is to provide an improved supersonic defect detection apparatus for pipe welds in which a contact medium, for example water, is circulated between the operating surface of the probe and a water tank so that it is not necessary to supplement the water and so that water contaminated by radioactive substances is not discharged to the outside when the apparatus is used to examine the welds of an atomic reactor.

Yet another object of this invention is to provide defect detection apparatus including guide means which permits smooth insertion of the apparatus into a pipe to be examined irrespective of the deformation or bending thereof.

A further object of this invention is to provide supersonic defect detection apparatus especially suitable for examining the welds of control rod housings of an atomic reactor which are vertically arranged in a closely spaced relationship.

According to one aspect of this invention there is provided a method of examining the weld of a vertical pipe by a supersonic wave, comprising the steps of inserting a supersonic probe into the pipe through the bottom opening thereof and raising the probe to a weld of the pipe to be examined.

According to another aspect of this invention there is provided supersonic defect detection apparatus for examining the weld of a vertical pipe, comprising means for revolving the probe along the inner surface of the vertical pipe, means removably connected to the lower end of the pipe for vertically driving the probe revolving means, and means connected to the vertically driving means for circulating a contact medium between the operating surface of the probe and a tank containing the contact medium.

The supersonic defect detection apparatus of this invention is especially suitable for examining the weld between the housing of a control rod driving mechanism and the flange of a boiling water type atomic reactor, as well as the welds between such housing and stub tubes from inside of the housing.

BRIEF DESCRIPTION OF THE DRAWINGS

In the accompanying drawings:

FIG. 3 is a longitudinal sectional view of a control rod housing showing the manner of welding it to the pressure vessel of an atomic reactor through a stub tube;

DESCRIPTION OF THE PREFERRED EMBODIMENT

Figure 1:
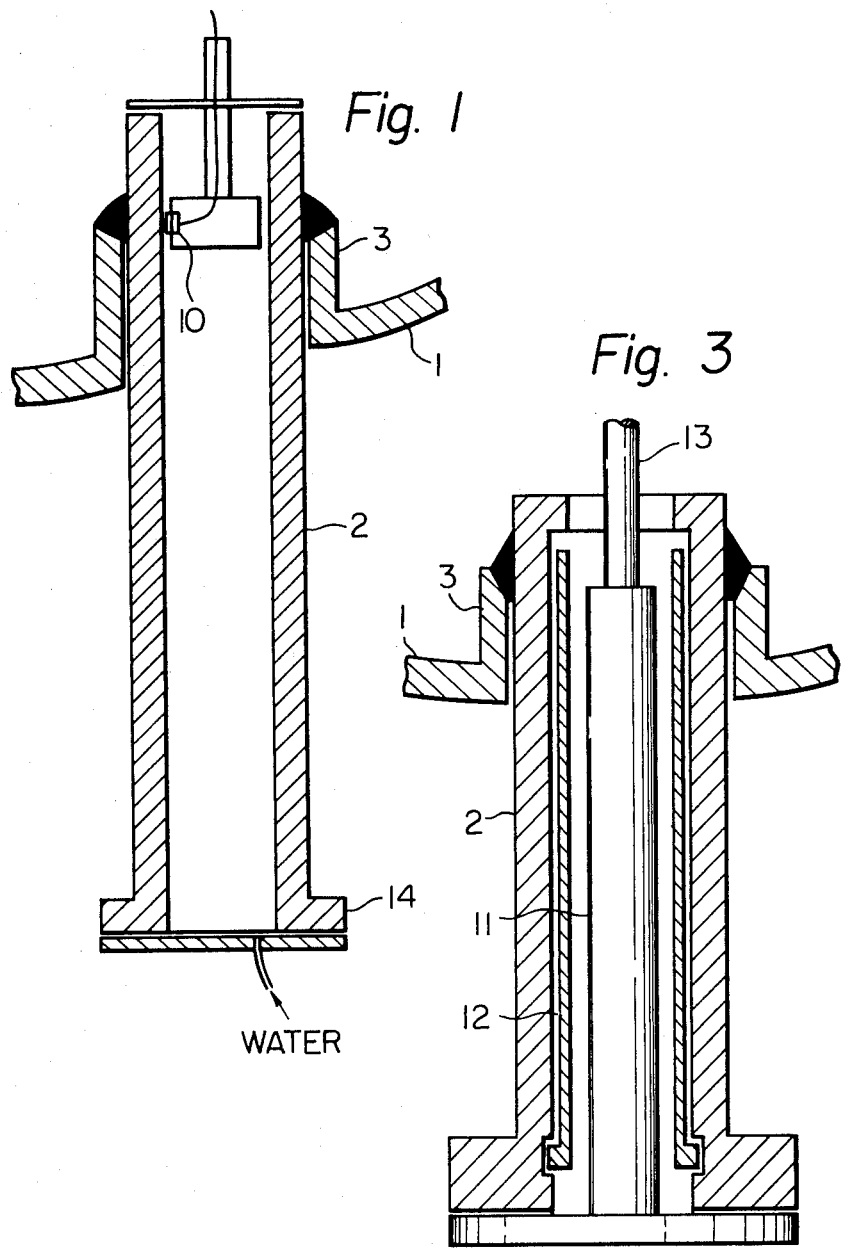
FIG. 1 is a longitudinal sectional view of a control rod housing showing the manner of inserting from above a probe head of a supersonic defect detection apparatus.
Figure 2:
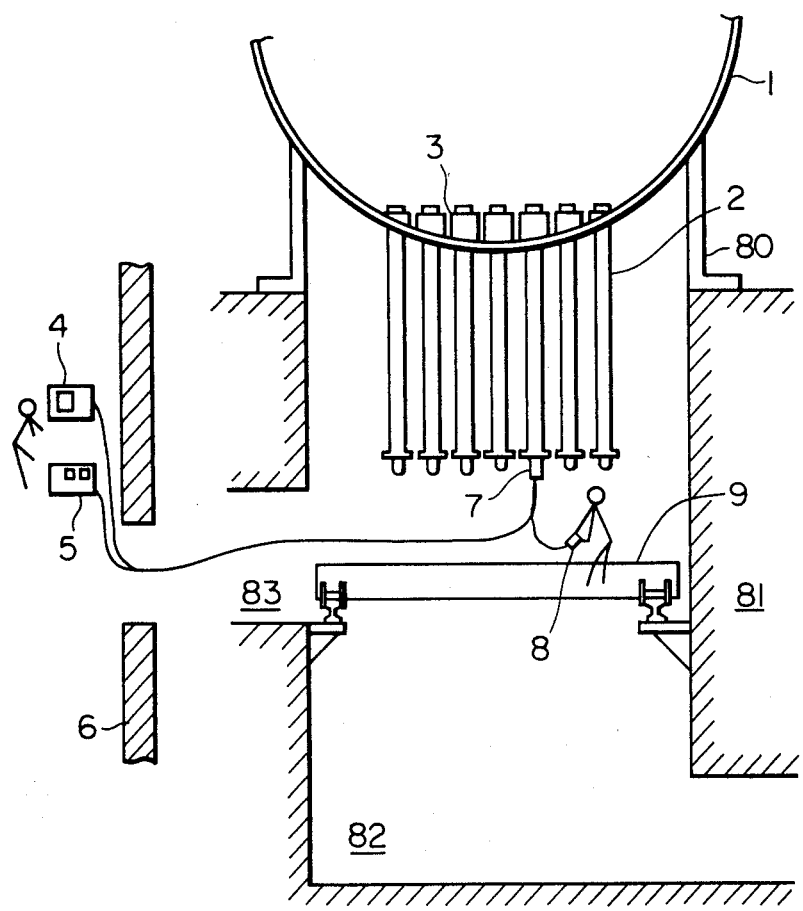
FIG. 2 is a diagrammatic representation showing the manner of remotely operating the supersonic defect detection apparatus for examining control rod housings of an atomic reactor from outside of the pressure vessel of the reactor.

As shown in FIGS. 1 and 2, the pressure vessel 1 of an atomic reactor is supported by a foundation 81 through a supporting skirt 80 which surrounds a plurality of housings 2 or pipes for control rods, not shown. The foundation 81 is formed with an operating pit 82 beneath the control rod housings 2. The pit contains a service platform 9 rotatable in the horizontal direction, and a side opening 83 on the same level as the service platform 9. As shown in FIG. 3 each control rod housing 2 is attached by a watertight weld to the pressure vessel 1 through a stub tube 3. Within the control rod housing 2 is disposed a thermal sleeve 12 which surrounds a control rod mechanism 11 with its lower end secured by bolts, not shown, to the lower flange of the control rod housing 2. Accordingly, to examine the weld between the control rod housing 2 and the stub tube 3 the control rod driving mechanism 11 must be removed.

Figure 4:
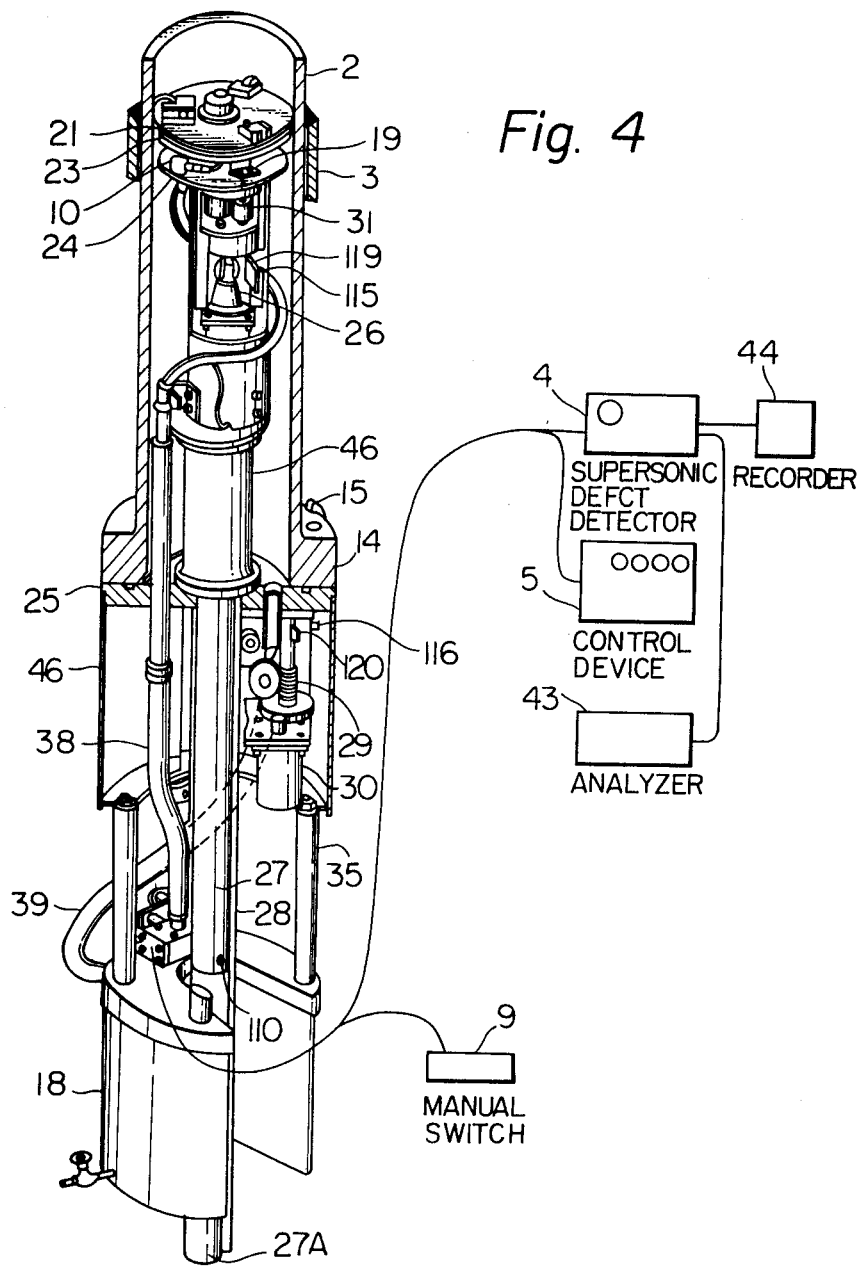
FIG. 4 is a perspective view showing the supersonic defect detection apparatus embodying the invention.

The supersonic defect detection apparatus utilized to examine these welds is shown in FIG. 4 and comprises vertically driving means, probe revolving means moved in the vertical direction by the vertically driving means, a probe 10 secured to the probe revolving means for detecting defects by ultrasonic waves and a water tank 18 for supplying water to a space between the probe 10 and a portion to be examined.

The vertically driving means comprises a flange 25 in contact with the flange 14 of the control rod housing 2 and having the same diameter as the latter flange, a first electric motor 30 secured to the lower surface of flange 25, a push up rod 27, a single rack 28 provided along the side surface of the push up rod, and a reduction gear train 29, for example a worm and worm wheel, meshing with the rack 28 for converting the rotary motion of the shaft of the motor 30 into a linear motion. The flange 25 is provided with a central perforation through which the push up rod 27 is movable in the vertical direction.

The probe revolving member is secured to the upper end of the push up rod 27 and comprises a second electric motor 26 secured to the upper end of the push up rod 27, and a speed reducer 31 connected to the rotor shaft of motor 26, the output shaft of the speed reducer being secured to the probe 10 through a pair of clamping discs 23 and 24. A guide disc 21 is mounted on the disc 23 for protecting and guiding the probe 10 when it is inserted into a pipe to be examined.

Figure 5:
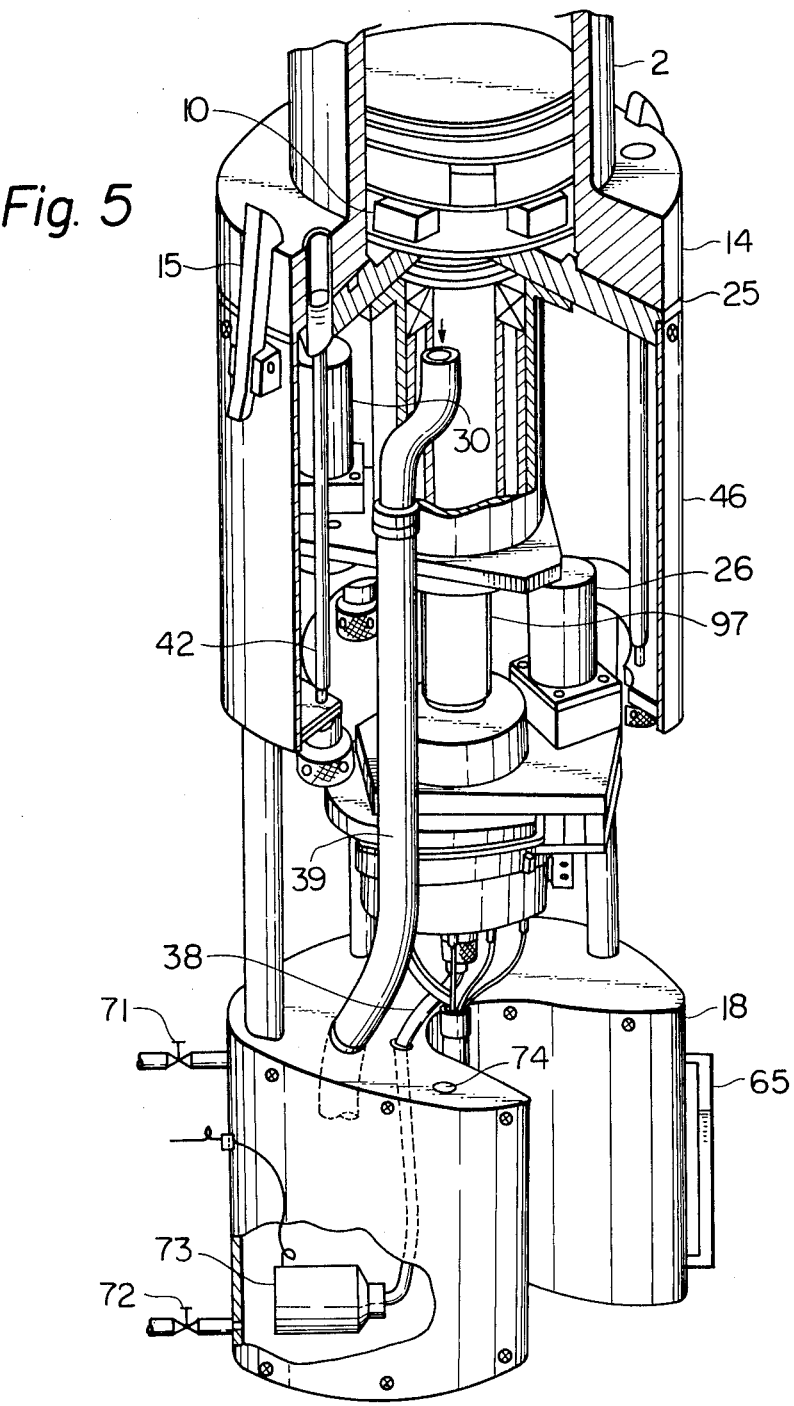
FIG. 5 is a perspective view, partly in section, showing a modified embodiment of this invention in which the motor for revolving the probe is secured on the outside of the control rod housing.

The water tank 18 is connected to the bottom of the vertically driving means through several connecting rods 35. As shown in FIG. 5, an immersion pump 73 is contained in the water tank 18. A water feed hose 38 is connected to the discharge port of the pump 73, and the other end of the hose extends upwardly through flange 25 and terminates near the probe 10. Accordingly, the water pumped by the pump 73 is discharged to the operating surface of the probe 10, and discharged through a drain pipe 39. (see FIG. 4)

The motor 30 of the vertically driving means is controlled by a manual switch 9 located near the detection apparatus or a control device 5 while the motor 26 for revolving the probe is controlled by the control device 5. The probe 10 is connected to a defect analyzer 43 and a recording device 44 via supersonic defect detector 4. A limit switch 19 is mounted on the disc 24, and a cylinder 46 is secured by a watertight connection to the upper surface of flange 25 to surround the push up rod 27 so as to prevent reactor water or water passing through the operating surface of the probe 10 from flowing through an opening accommodating the push up rod.

The angular position of the probe is displayed in degrees by operating a reed switch 115 by a permanent magnet 119 secured to the shaft of motor 26, while the vertical position is displayed in millimeters by operating a reed switch 116 by a permanent magnet 120 secured to the shaft of the vertically driving motor 30.

The apparatus is mounted as follows. At first, the control rod driving mechanism 11 and the thermal sleeve 12 (shown in FIG. 3) are removed from the control rod housing 2 and then the apparatus is mounted in the housing 2. At this time, the apparatus is temporarily held by hooks 15 mounted on the periphery of flange 25 and then permanently secured by bolts which are identical to those utilized to clamp the control rod mechanism 11. Thereafter, switch 9 is closed for pushing up the push up rod 27 to be pushed up by motor 30 and probe 10 raised to a predetermined position; that is to the weld between the control rod housing 2 and the stub tube 3. Then the probe 10 is revolved along the weld by motor 26. At the same time, immersion pump 73 is operated to supply water to the operating surface of the probe. While the probe is being revolved the vertically driving means is moved upwardly or downwardly, to examine the weld. This operation is repeated to examine the entire weld. The water flowing along the operating surface of the probe is returned to tank 18 through drain pipe 39 for recirculation.

As above described, the apparatus constructed to examine a weld of a vertical pipe can be readily mounted and dismounted from the pipe in a short time. Accordingly irradiation of the operator by radioactive rays can be minimized. Further, as the apparatus is secured by bolts identical to those used to secure the control rod mechanism it is possible to adjust the origin and to mount always in the same position thus making easy and accurate comparative analysis of the result of examination. Further, the water or reactor water passing along the operating surface of the probe is recirculated through a water tank so that it is not necessary to supplement water and the total pressure of the reactor water does not act upon the apparatus thereby decreasing the weight thereof.

During the construction of an atomic power plant, examination of the weld between the stub tube at the lower portion of the pressure vessel and the control rod housing is performed by lowering from above the probe 10 to the weld as shown in FIG. 1. This method, however, is not only troublesome but also requires removal of the fuel assembly, during periodic examinations. During the construction of the plant, since a number of welders are operating beneath the pressure vessel and since strict tests of various dimensions are made for high degrees of accuracy of the welded assembly, many workmen are engaging for many types of work. Further, after completion of the plant, in view of the danger of irradiation, the examination by an operator inside of the pressure vessel should be avoided. In contrast, the apparatus of this invention can be inserted into the control rod housing through the bottom thereof. Accordingly, it is not necessary for the operator to enter into the pressure vessel contaminated with radioactive substances.

As shown in FIG. 1, in certain cases the flange 14 is welded to the lower end of the control rod housing 2. During fabrication, such weld is usually examined by X-rays but once the operation of the atomic power plant is started such method of examination cannot be used due to the danger of radioactive radiation. For this reason, a supersonic defect detector is suitable. To examine such weld, in the same manner as above described, control rod mechanism 11 and the thermal sleeve 13 shown in FIG. 3 are removed.

Figure 6:
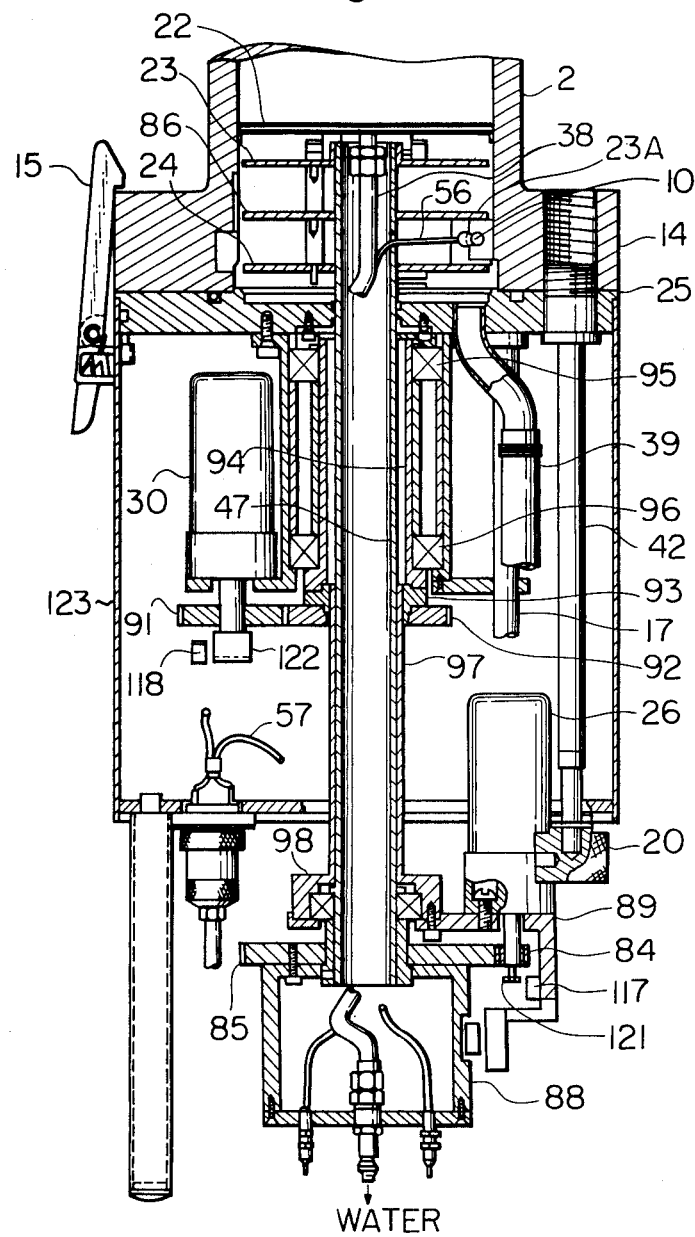
FIG. 6 is a sectional view of the modified embodiment shown in FIG. 5.

In a modification shown in FIGS. 5 and 6, a mechanism is used to move the probe in the vertical direction. This modification can also be used to examine horizontal pipes.

This supersonic defect detection apparatus is also mounted on the flange 14 of the control rod housing by using hooks 15 as in the previous embodiment.

The water tank 18 is removable as shown in FIG. 6. Revolution of the probe 10 is effected by a motor 26 through a gear 84 secured to the motor shaft and a gear 85 secured to the vertical hollow shaft 47. Discs 23, 23A and 24 which supports the probe 10 are rotated by shaft 47. The gear 85 supports a cable support 88 which supports cables leading to the probe, and the water supply pipe.

The base 89 of the motor 26 is provided with perforations for receiving guide rods 17 so that the motor 26 can move in the vertical direction along the guide rods 17 which are secured to flange 25.

The vertical movement of the probe 10 is effected by motor 30. Thus, a gear 91 is secured to the shaft of the motor to mesh a gear 92 for operating a threaded bushing 93. The inner surface of the bushing 93 is threaded so that it is rotated together with a bearing support 94. Since the bearing support and the threaded bushing are supported by flange 25 through bearings 95 and 96 they can rotate but can not move in the vertical direction.

When the threaded bushing 93 rotates, a pipe 97 provided on its outside with threads meshing the threads on the inner surface of the bushing tends to rotate. But as the threaded pipe 97 is integral with a cup shaped head 98 secured to the base 89 of the motor 26, and since the base 89 can move only in the vertical direction along the guide rods 17 the threaded pipe 97 is moved in the vertical direction. There is no thread on the inner surface of the pipe 97. In FIG. 6, this pipe is shown in its lowest position.

Display of the angular position of the probe is made in terms of one degree by operating reed switch 117 by permanent magnet 121 secured to the shaft of motor 26, and the display of axial movement is made in terms of 0.1 mm by operating a reed switch 118 by a permanent magnet 122 secured to the shaft of motor 30.

Instead of mounting the detection apparatus on the lower side of a vertical pipe, it can also be mounted on the upper side of the pipe.

As in the previous embodiment the probe is raised to a weld to be examined by operating the motor 30 by a manual switch or a remote control device. Whether the probe has reached the weld or not is judged by detecting a digital signal generated by the control device or a reflected echo of the supersonic wave.

When the probe has reached the weld to be examined, the probe is revolved by motor 26. The examination can be made by revolving the probe in one horizontal plane and then in different horizontal planes or moving the probe vertically at a peripheral position and then vertically at other peripheral positions. Such examination can be made manually or automatically.

It is possible to mount a plurality of probes, for example ten units, on the shaft 47 and to operate some of them to transmit and receive supersonic wave with a time difference. Except for the mounting and dismounting operations, the operator is not required to approach the control rod housing contaminated with a radioactive substances. Where a plurality of probes are mounted on the same shaft it is not necessary to change the number of probes. Further, the apparatus can be automatically operated from a remote position by a single operator, so that it is possible to prevent errors caused by manual operations by several operators. Evaluation and analysis of the result of examination can also be made automatically. Circulation of the contact medium such as water and oil eliminates the trouble of admitting the medium into the pipe to be examined at each examination and prevents contamination caused by the spent medium. Further it is possible to save time required to fill the pipe up to the probe. Where the vertical pipe has a length of several meters and when water is fed into the pipe from bottom, it takes a long time before the pipe is filled with water.

As will be described later, according to this invention water is caused to flow only through the space between the inner surface of the pipe to be examined and the operating surface of the probe.

The water contacting the cable connector causes leakage of current which generates noise. According to this invention, it is not necessary to immerse in water the entire portion of the probe, and after use the water falls down along the inner wall of the pipe so that leakage of current noise can be prevented.

The length of the shaft for vertically moving the probe often amounts to 4 to 7 meters. In such case the shaft can be fabricated by connecting short sections. Although these sections can be connected together by a threaded coupling, since substantially no tension is applied to the shaft, the sections may be connected by a friction coupling or a simple pin. More particularly, it is necessary to construct the portion of shaft 27 above coupling pin 110 shown in FIG. 4 as an integral body because motors 26, 30 and various gears are provided for this section. However, as the pipe to be examined is long as above described, it is inconvenient to construct the shaft 27 to have the same length as the length of the pipe to be examined. According to this invention, any number of sections 27A can be connected in succession to provide the required length. Such multisection construction facilitates transportation of the parts onto the service platform 9 through side opening 83 (see FIG. 2). When these sections and shaft 27 are coupled together by frictional couplings, they can slide relatively in the axial direction when subjected to an excessive force.

By providing a suitable cable support it is possible to prevent twisting and tangling of the cable leading to the probe when it is revolved.

Figure 7:
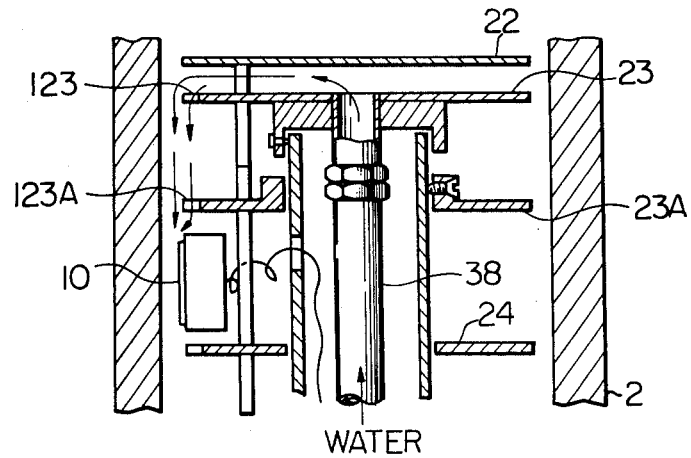
FIG. 7 is a partial longitudinal sectional view showing the manner of supplying water to the probe.

In a case shown in FIG. 7 water supplied from the pump through pipe 38 flows radially on the upper surface of disc 23 and then downwardly along the inner surface of the control rod housing 2. Discs 23 and 23A are provided with notches 123 and 123A above the probe 10 so as to cause the water to flow between the housing 2 and the probe 10. Thus, the probe and its cable are not entirely immersed in water. A baffle disc 22 is provided above disc 23 to direct water issuing from pipe 38 toward the inner surface of the control rod housing 2.

Figure 8:
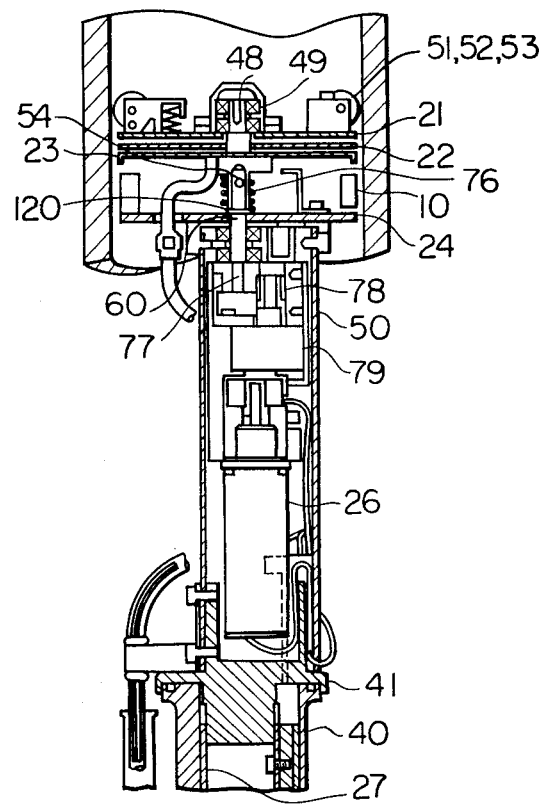
FIG. 8 is a longitudinal sectional view of a modified embodiment of this invention in which the motor for revolving the probe is contained in a tube.
Figure 9:
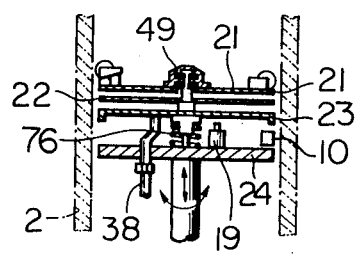
FIG. 9 is a sectional view showing the supporting and guiding device of the probe.

In a modified embodiment shown in FIG. 8, motor 26 for revolving the probe 10 is contained in a tube 50 which is connected to driving shaft 27 through an intermediate stub shaft 41. Thus, the tube 50 and probe 10 are moved in the vertical direction by the driving shaft 27. A bushing 40 for preventing water leakage is supported at its bottom.

The rotation of the motor 26 is transmitted to gear 77 through a speed reducer 79 and a gear 78 meshing gear 77. The gear 77 is connected to shaft 60 which revolves the probe 10 through disc 24. Shaft 60 is connected to shaft 120 of disc 23 through a pin 54.

The construction and operation of various elements mounted on disc 21 will be described later with reference to FIGS. 9 to 12.

According to this embodiment since the vertically movable shaft 27 and the shaft for revolving the probe are constructed as independent members and the motor 26 for revolving the probe is contained in non-rotating tube 50 it is possible to readily handle the detection apparatus. Further, since the motor for revolving the probe is contained in the tube it is possible to reduce its torque and decrease noise coming into the detected signal of the detection apparatus.

Figure 10:
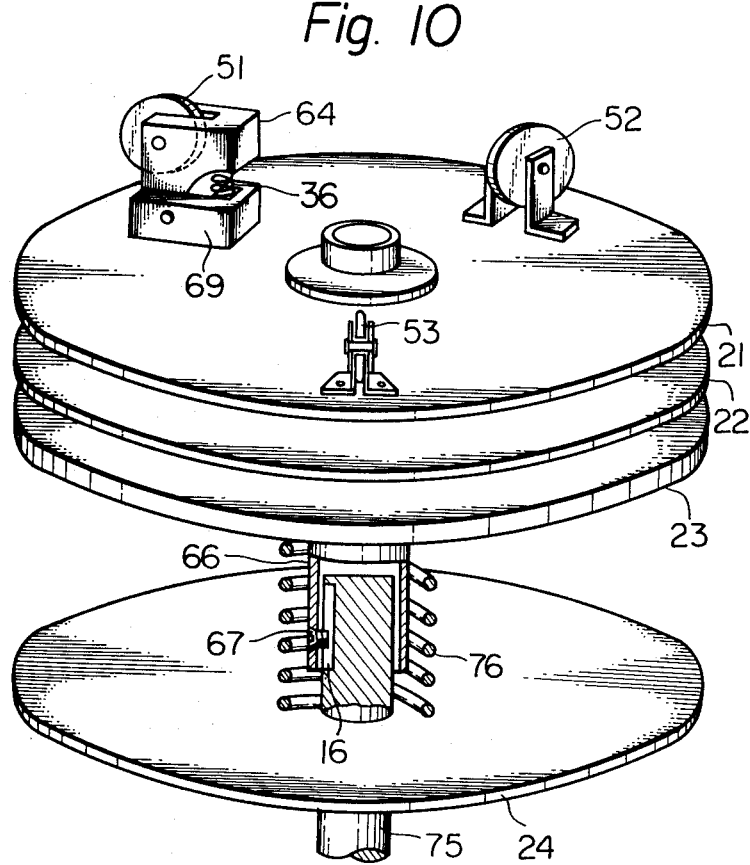
FIG. 10 is an exploded view of the device shown in FIG. 9.
Figure 11:
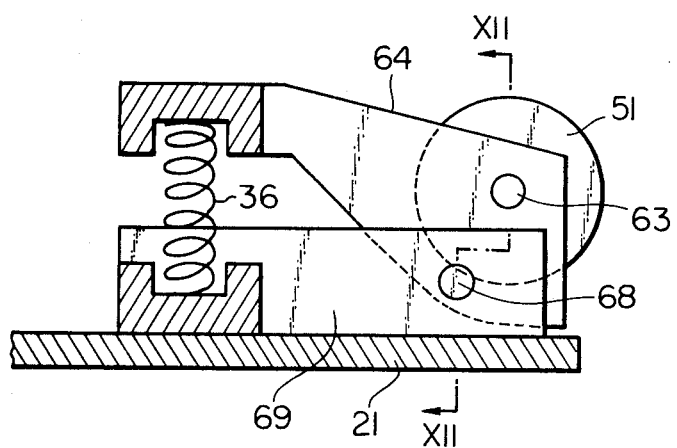
FIG. 11 is a side view showing a spring biased guide wheel of the probe supporting and guiding device shown in FIGS. 9 and 10.
Figure 12:
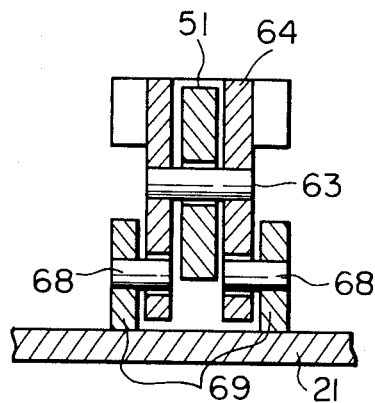
FIG. 12 is a sectional view of the device shown in FIG. 11 taken along a line XII — XII.

FIGS. 9 through 12 show the detail of the supporting and guiding device of the probe. As shown, this device comprises disc 24 which revolves and moves in the vertical direction, a water seal disc 23 mounted above disc 24 and the probe 10 supported thereby. The disc 23 is biased by compression spring 76. The supporting and guiding device further comprises a disc 21 rotatably mounted above disc 23. The hollow shaft 66 of disc 23 is connected to shaft 75 of disc 24 through a key way 16 provided for shaft 75 and a pin 67 secured to the hollow shaft 66. The guide disc 21 is rotatably mounted on the water seal disc 23 through a thrust bearing 49. Three equally spaced guide rollers 51, 52 and 53 are mounted on the disc 21. Two of the guide rollers, that is 52 and 53 are securely mounted on the disc 21 but the remaining roller 51 is supported by a resilient support so that it can move in the radial direction of the disc 21. As shown in FIGS. 10 and 12, the resilient support comprises U shaped supporting member 69 secured to the upper surface of the disc 21, a U shaped lever 64 supported by the supporting member 69 through pins 68, guide roller 51 supported by lever 64 through a pin 63 and a spring 36 interposed between the lever 64 and the supporting member 69. Pins 63 and 68 are located at different distances from the guide disc 21. The limit switch 19 is positioned between discs 23 and 24. When this limit switch operates, the elevating motion of the disc 23 is stopped.

Three guide rollers prevent the probe 10 from being damaged when it is revolved or moved in the vertical direction. Since one guide roller 51 can move in the radial direction of the disc 21 this arrangement can absorb difference in the inside diameter of a pipe to be examined caused by deformation or bending of the pipe, thus assuring smooth insertion of the defect detection apparatus. Further, limit switch 19 prevents excessive insertion. During the revolution of the probe the guide roller 51 is resiliently urged against the inner surface of the pipe so that the guide disc 21 is maintained stationary. Further, three guide rollers hold the disc 21 at the correct center position thus facilitating ready revolution of the probe. Summarizing the above this invention has the following advantages.

1. Mounting and dismounting of the supersonic defect detection apparatus can be made readily and in a short time. This feature is especially advantageous when the apparatus is used to examine welds of control rod housings of an atomic reactor where irradiation of radioactive substances is severe. With the apparatus of this invention, the safety of the operator can be improved.

2. The apparatus is inserted into a pipe such as a control rod housing from the botton thereof. According to this feature the operator is not required to enter into the pressure vessel as in the prior art apparatus which was inserted into the control rod housing from the inside of the pressure vessel.

3. As the water supplied to the operating surface of the supersonic probe is circulated through a water tank, it is not necessary to supplement water to the circulating system. With this arrangement, the total pressure of the reactor water does not act upon the detection apparatus so that it is not necessary to construct the apparatus to be rugged. Moreover, there is no fear of discharging to the outside spent water contaminated by radioactive substances.

4. As the motor for revolving the probe is contained in a hollow tube and this tube is connected to a shaft for vertically moving the probe the overall weight of the driving device can be reduced. Moreover as the motor is not provided on the outside of the driving device, the workability of the apparatus can be improved because in an atomic reactor many control rod housings are closely disposed.

5. The apparatus can be remotely operated, thus improving the safety of the operator. Where the evaluation and analysis of the result of examination are automated, examination of a number of welds can be accelerated.

6. When mounting the apparatus on the flange of a control rod housing, the apparatus is temporarily supported by hooks and then secured to the flange with bolts identical to those used to assemble the apparatus so that centering of the apparatus is easy.

7. A plurality of probe guide rollers are used, one of which is resiliently supported to be movable in the radial direction so that it is possible to smoothly insert the apparatus into a pipe to be examined irrespective of its deformation or bending. Moreover, it is possible to maintain the probe always at the center of the pipe to be examined.

8. As the shaft 27 for raising the probe is made of a plurality of sections that can be readily coupled together, transportation of these members to the service platform beneath the pressure vessel and the assembling operation of these members on the service platform are greatly facilitated.

We claim:
1. Supersonic defect detection apparatus for examining the weld of a vertical pipe comprising:
a supersonic probe, means for revolving said probe along the inner surface of said vertical pipe, said probe revolving means including a first disc mounted on a rotary shaft, means removably connected to the lower end of said pipe for vertically driving said probe revolving means, means connected to said vertically driving means for circulating contact liquid between the operating surface of said probe and a tank containing said contact liquid, and means for supplying said contact medium onto said first disc including a baffle plate mounted above said first disc for directing said contact liquid in the radial direction of said first disc, said probe being positioned beneath said first disc near the periphery thereof, and said first disc being provided with a notch above said probe for guiding the contact liquid between the operating surface of said probe and the inner wall of said pipe to be examined.

2. The apparatus according to claim 1 wherein said vertically moving means comprises a second disc for supporting said probe, said rotary shaft having one end connected to said second disc and the other end provided with a gear, a first electric motor for driving said gear, a pipe coupled to said rotary shaft and a second electric motor for driving said pipe in the vertical direction.

3. The apparatus according to claim 2 wherein said first electric motor is located near the coupling point between said rotary shaft and said pipe.

4. The apparatus according to claim 1 wherein said vertically driving means comprises a first shaft section carrying said probe and at least one additional shaft section removably coupled to said first shaft section.

5. The apparatus according to claim 1 wherein said probe revolving means comprises a second disc secured to said rotary shaft for supporting the probe, a third disc rotatably mounted on said rotary shaft a predetermined distance from said first disc, a plurality of guide rollers mounted on said third disc, and a resilient support for supporting one of said guide rollers to be movable in the radial direction of said third disc.

6. The apparatus according to claim 5 which further comprises a limit switch located between said first and second discs for limiting the upward movement of said rotary shaft to stop the elevation of said first disc.

7. The apparatus according to claim 1 wherein said vertical pipe is provided with a flange at its lower end and said apparatus further comprises spring biased hooks pivotally mounted on said vertically driving means and adapted to engage said flange for supporting said apparatus.

8. The apparatus according to claim 1 wherein said probe revolving means further comprises a guide disc rotatably mounted on said baffle plate, a plurality of guide rollers mounted on the periphery of said guide disc and resilient means for urging at least one of said guide rollers against the inner wall of said pipe.

9. The apparatus according to claim 1 wherein said means for vertically driving the probe comprises a flange removably connected to the lower end of said pipe, a push up rod for supporting said probe and said means for revolving the same, said push up rod extending through said flange, a first electric motor suspending from said flange for driving said push up rod in the axial direction thereof, and said probe revolving means comprises a second electric motor mounted on the upper end of said push rod.

10. The apparatus according to claim 1 wherein said means for revolving said probe comprises a flange removably connected to the lower end of said pipe, a hollow vertical shaft extending through said flange for supporting said probe, a first electric motor suspending from said flange for driving said hollow vertical shaft in the axial direction thereof, and a second electric motor also suspending from said flange for rotating said hollow vertical shaft.

11. The apparatus according to claim 10 wherein a pipe for supplying said contact medium and lead wires connected to said probe extends through the inside of said vertical hollow shaft.

12. The apparatus according to claim 10 which further comprises a cylindrical cover which surrounds said first and second electric motors and said hollow vertical shaft, and means for securing the upper end of said cylindrical cover to the periphery of said flange.

13. The apparatus according to claim 1 which further comprises a hollow tube connected between the upper end of said vertically driving means and said probe, and wherein an electric motor for revolving said probe is contained in said hollow tube.

* * * * *